United States Patent
Manuel et al.

(10) Patent No.: US 9,974,585 B2
(45) Date of Patent: May 22, 2018

(54) ARTICLES COMPRISING REVERSIBLY ATTACHED SCREWS COMPRISING A BIODEGRADABLE COMPOSITION, METHODS OF MANUFACTURE THEREOF AND USES THEREOF

(71) Applicant: UNIVERSITY OF FLORIDA RESEARCH FOUNDATION, INC., Gainesville, FL (US)

(72) Inventors: Michele Viola Manuel, Gainesville, FL (US); James F. Schumacher, Alpharetta, GA (US); Emily Hester, Orlando, FL (US); Daniella C. van der Merwe, Palm Harbor, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days. days.

(21) Appl. No.: 15/711,452

(22) Filed: Sep. 21, 2017

(65) Prior Publication Data
US 2018/0008328 A1    Jan. 11, 2018

Related U.S. Application Data

(63) Continuation of application No. 15/033,182, filed as application No. PCT/US2014/064065 on Nov. 5, 2014, now Pat. No. 9,795,427.

(Continued)

(51) Int. Cl.
*A61F 5/00*    (2006.01)
*A61B 17/86*    (2006.01)
(Continued)

(52) U.S. Cl.
CPC ........ *A61B 17/8605* (2013.01); *A61C 8/0012* (2013.01); *A61C 8/0022* (2013.01);
(Continued)

(58) Field of Classification Search
None
See application file for complete search history.

(56) References Cited

U.S. PATENT DOCUMENTS

| 4,713,004 A | 12/1987 | Linkow |
| 4,791,929 A | 12/1988 | Jarrett |

(Continued)

FOREIGN PATENT DOCUMENTS

| EP | 2014319 A1 | 1/2009 |
| EP | 2022443 B1 | 2/2009 |
| WO | WO2011105685 A2 | 9/2011 |

OTHER PUBLICATIONS

Berglund, Ida S., et al.; "Synthesis and Characterization of Mg—Ca—Sr Alloys for Biodegradable Orthopedic Implant Applications"; Society for Biomaterials; Jun. 12, 2012; pp. 1524-1534.

(Continued)

*Primary Examiner* — Sameh Boles
(74) *Attorney, Agent, or Firm* — Thomas Horstemeyer LLP

(57) ABSTRACT

Disclosed herein is an article comprising a first screw and a second screw, the first screw being reversibly attached to the second screw such that a longitudinal axis of the first screw coincides with or is parallel to a longitudinal axis of the second screw; the first screw and the second screw each comprising a biodegradable composition, the biodegradable composition comprising a metal or metal alloy comprising magnesium, strontium, zinc, calcium or a combination comprising at least one of the foregoing. Methods of making and using the article are also disclosed herein.

16 Claims, 1 Drawing Sheet

Related U.S. Application Data

(60) Provisional application No. 61/900,055, filed on Nov. 5, 2013.

(51) Int. Cl.
*A61F 2/02* (2006.01)
*A61C 8/00* (2006.01)
*A61B 17/00* (2006.01)

(52) U.S. Cl.
CPC ...... *A61F 2/02* (2013.01); *A61B 2017/00526* (2013.01); *A61C 8/0074* (2013.01); *A61F 2210/0004* (2013.01)

(56) References Cited

U.S. PATENT DOCUMENTS

| | | |
|---|---|---|
| 6,896,517 B1 | 5/2005 | Bjoern |
| 7,771,774 B2 | 8/2010 | Berckmans, III |
| 8,197,480 B2 | 6/2012 | Roller et al. |
| 8,968,002 B2 | 3/2015 | Purga |
| 2003/0087197 A1 | 5/2003 | Schulman |
| 2004/0241314 A1 | 12/2004 | Li |
| 2005/0079200 A1 | 4/2005 | Rathenow |
| 2005/0250073 A1 | 11/2005 | Tresser |
| 2005/0266041 A1 | 12/2005 | Gerold et al. |
| 2006/0198869 A1 | 9/2006 | Furst et al. |
| 2008/0118893 A1 | 5/2008 | Armellini |
| 2008/0243242 A1 | 10/2008 | Kappelt |
| 2008/0312736 A1 | 12/2008 | Mueller |
| 2009/0131540 A1 | 5/2009 | Hiromoto |
| 2009/0226857 A1 | 9/2009 | Grant |
| 2010/0075162 A1 | 3/2010 | Yang et al. |
| 2010/0106243 A1 | 4/2010 | Wittchow |
| 2010/0161031 A1 | 6/2010 | Papirov et al. |
| 2011/0054629 A1 | 3/2011 | Seok et al. |
| 2011/0076319 A1 | 3/2011 | Orlowski et al. |
| 2011/0319986 A1 | 12/2011 | Bayer |
| 2014/0154341 A1 | 6/2014 | Manuel |

OTHER PUBLICATIONS

Bornapour, M., et al.; "Biocompatibility and Biodegradability of Mg—Sr Alloys: The Formation of Sr-Substituted Hydroxyapatite"; Acta Biomaterialia vol. 9 (2013); Aug. 5, 2012; pp. 5319-5330.

Brar, et al. "Investigation of the mechanical and degradation properties of Mg—Sr and Mg—Zn—Sr alloys for use as potential biodegradable implant materials." Journal of the Mechanical Behavior of Biomedical Materials 7 (2012) 87-95.

Brar, H. S. et al. "A study of biodegradable Mg—3Sc—3Y alloy and the effect of surface passivation on in-vitro degradation" Acta Biomaterialia 9 (2013) 5331-5340.

Chen SL, Daniel S, Zhang F, Chang YA, Yan XY, Xie FY, Schmid-Fetzer R, Oates WA. "The PANDAT Software Package and its Applications" CALPHAD 2002; 26: (175-188).

International Preliminary Report on Patentability for Application No. PCT/US2011/042892 Filing Date Jul. 2, 2011; dated Jan. 8, 2013 (6 pages).

International Search Report for Application No. PCT/US2011/042892 Filing Date Jul. 2, 2011; dated Mar. 20, 2012 (4 pages).

International Search Report for Application No. PCT/US2014/045364 Filing Date Jul. 3, 2014; dated Oct. 28, 2014 (6 pages).

International Search Report for Application No. PCT/US2014/064065 Filing Date Nov. 5, 2014; dated Feb. 18, 2015 (8 pages).

Li Z, Gu X, Lou S, Zheng Y. "The development of binary Mg—Ca alloys for use as biodegradable materials within bone" Biomaterials 2007; 29: (1329-1344).

Wan Y, Xiong G, Luo H, He F, Huang Y, Zhou X. "Preparation and characterization of a new biomedical magnesium-calcium alloy" Materials & Design 2008; 29: (2034-2037).

Written Opinion for Application No. PCT/US2011/042892 Filing Date Jul. 2, 2011; dated Mar. 20, 2012 (5 pages).

Written Opinion for Application No. PCT/US2014/064065 Filing Date Nov. 5, 2014; dated Feb. 18, 2015 (5 pages).

Written Opinion for International Application No. PCT/US2014/045364 Filing Date Jul. 3, 2014; dated Oct. 28, 2014 (9 pages).

ARTICLES COMPRISING REVERSIBLY ATTACHED SCREWS COMPRISING A BIODEGRADABLE COMPOSITION, METHODS OF MANUFACTURE THEREOF AND USES THEREOF

CROSS-REFERENCE TO RELATED APPLICATIONS

This application is a continuation of U.S. patent application entitled "ARTICLES COMPRISING REVERSIBLY ATTACHED SCREWS COMPRISING A BIODEGRADABLE COMPOSITION, METHODS OF MANUFACTURE THEREOF AND USES THEREOF" having Ser. No. 15/033,182, having a filing date of Apr. 29, 2016, which claims priority and benefit of International Application No. PCT/US14/064065 having a filing date of Nov. 5, 2014 which claims the benefit of U.S. Application No. 61/900,055 filed on Nov. 5, 2013, the entire contents of which are hereby incorporated by reference.

BACKGROUND

This disclosure relates to articles comprising reversibly attached screws comprising a biodegradable composition, methods of manufacture thereof and uses thereof.

Orthopedic implants are medical devices which are surgically implemented in order to repair/support an injury to a bone or to replace a damaged bone in a living being. Implementation of the implant, also known as "internal fixation", anchors the bones in which they are implanted, thereby facilitating healing of the injury.

Non-biodegradable implants suffer from various drawbacks. Non-biodegradable implants may present biocompatibility concerns over time if the implant is not removed from the living being. Non-biodegradable implants may also involve a second surgical procedure in order to remove the implant after healing is complete. Non-biodegradable implants (e.g., titanium implants) may also be significantly stronger than the bone in the living being in which they are employed. This difference between the strength of the bone compared to the relative strength of the implant leads to stress shielding. Stress shielding occurs when the implant bears bodily stress, rather than sharing the bodily stress with the bone, due to the much higher relative strength of the implant. Stress shielding in turn leads to bone atrophy.

Biodegradable orthopedic implants may avoid biocompatibility issues; however, biodegradable implants which are based upon polymers have significantly lower strength than non-biodegradable implants. Such biodegradable implants also have a high degradation rate and/or degradation is incomplete, resulting in an undesirable residual pool. Biodegradable orthopedic implants are thus limited to low-load implant applications. Biodegradable implants may also employ specialized equipment, surface pre-treatments and/or simplified substrate geometries.

It is therefore desirable to develop an article which avoids the above-described problems, reduces stress shielding, improves stress sharing, is suitable in high-load applications, does not form a residual pool after degradation, is produced without specialized equipment, surface pre-treatments and/or restricted substrate geometries and/or positively influences bone growth and/or the healing process, when the article is used in the body of a living being.

SUMMARY OF INVENTION

Disclosed herein is an article comprising a first screw; and a second screw, the first screw being reversibly attached to the second screw such that a longitudinal axis of the first screw coincides with or is parallel to a longitudinal axis of the second screw; the first screw and the second screw each comprising a biodegradable composition, the biodegradable composition comprising a metal or metal alloy comprising magnesium, strontium, zinc, calcium, or a combination comprising at least one of the foregoing.

Disclosed herein too is a method comprising molding a first screw; and molding a second screw, the first screw being reversibly attached to the second screw such that a longitudinal axis of the first screw coincides with or is parallel to a longitudinal axis of the second screw, wherein the first and/or second screw comprises a biodegradable composition, which comprises a metal or a metal alloy comprising magnesium, strontium, zinc, calcium, or a combination comprising at least one of the foregoing.

Disclosed herein too is a method comprising disposing in the body of a living being an article comprising a first screw; and a second screw, the first screw being reversibly attached to the second screw such that a longitudinal axis of the first screw coincides with or is parallel to a longitudinal axis of the second screw; wherein the first screw and the second screw comprise a biodegradable composition, the biodegradable composition comprising a metal or metal alloy comprising magnesium, strontium, zinc, calcium, or a combination comprising at least one of the foregoing.

DETAILED DESCRIPTION

Disclosed herein is an article (e.g., a medical or dental implant) that comprises a biodegradable composition comprising a metal or a metal alloy. In an embodiment, the article comprises a first screw and a second screw, the first screw being reversibly attached to the second screw such that a longitudinal axis of the first screw coincides with a longitudinal axis of the second screw. Torque applied to the first screw is transmitted to the second screw to secure parts of the body (e.g., bones) together. Both screws are then absorbed into the body of a living being without any contamination of surrounding tissue or without any adverse effects to the body. In an embodiment, the article comprises a non-biodegradable portion and biodegradable portion that comprises the biodegradable composition. The biodegradable portion may be a coating or may be an integral part of the article.

The biodegradable article promotes healing, e.g., bone growth, at the implantation site when the article is disposed inside the body of a living being. The use of the biodegradable composition enhances the biocompatibility of the article and/or promotes healing following implantation of the article until the biodegradable composition is eventually degraded. The biodegradable composition thus provides a temporary enhancement to the article during a targeted duration of time following implantation of the article. The biodegradable composition may also be used to improve the biocompatibility of electronic circuit components in medical devices such as pacemakers.

Disclosed herein too is a method comprising molding a first screw and molding a second screw. The first screw is reversibly attached to the second screw such that a longitudinal axis of the first screw coincides with or is parallel to a longitudinal axis of the second screw, wherein the first and/or second screw comprises the biodegradable composition. Disclosed herein too is a method comprising disposing the article described herein in the body of a living being.

Figure 1:
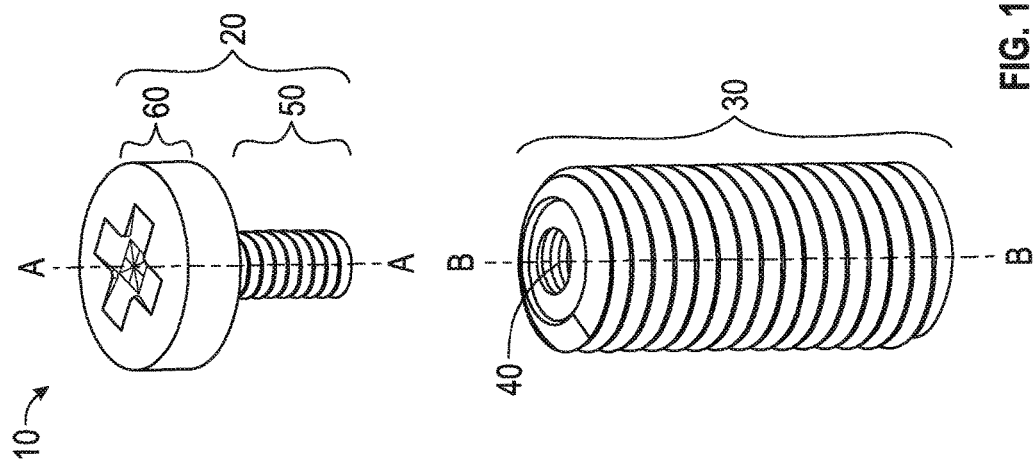
FIG. 1 is a side view of the assembly of a first screw and a second screw in an article according to an embodiment of the invention.

Referring to FIG. 1, the article 10 comprises a first screw 20 and a second screw 30, the first screw 20 being reversibly attached to the second screw 30 such that a longitudinal axis A-B of the first screw 20 coincides with a longitudinal axis A-B of the second screw 30. The longitudinal axis A-B extends longitudinally along the length of the first screw 20 and the second screw 30, respectively. As may be seen by reference to FIG. 1, the first screw 20 is concentrically disposed in the second screw 30, i.e., a longitudinal axis of the first screw 20 coincides with the longitudinal axis of the second screw 30. In an embodiment, the first screw 20 is eccentrically disposed in the second screw 30, i.e., a longitudinal axis of the first screw 20 is parallel to the second screw 30, but not coincident with it. The second screw 30 has a threaded hole 40 which is of sufficient size to accommodate the first screw 20. The first screw 20 further comprises a first screw shaft 50 and a screw head 60. The screw head 60 is adapted to be screwed into the second screw 30 using a tool (e.g., a screwdriver) which is complimentary to the shape of the screw head 60. The second screw 30 does not have a screw head, but has threads in the threaded hole 40 that are adapted to receive the first screw 20.

In an embodiment, the longitudinal axis of the first screw 20 is parallel to the longitudinal axis of the second screw 30. In yet another embodiment, the longitudinal axis of the first screw 20 is inclined at an angle other than 0° relative to the longitudinal axis of the second screw 30.

In an embodiment, the ratio of the (outer) diameter of the first screw shaft 50 to the (outer) diameter of the second screw 30 is 1:2 to 1:10, or 0.5 to 0.8.

In an embodiment, the length of the first screw shaft 50 is equal to or less than one-half, specifically equal to or less than one-third, and more specifically equal to or less than one-quarter of the length of the second screw 30.

Referring to FIG. 1, the first screw shaft 50 and the second screw 30 are each threaded. The second screw 30 is threaded in a manner to accommodate the threading on the first screw shaft 50. The second screw 30 is also threaded. The thread pitch is selected such that the threads have a relatively thick profile while maintaining a minimal surface area. The thread pitch is also selected such that degradation rate of the traders in comparison to the overall article is not adversely affected.

Various types of threads may be employed. Non-limiting examples of such threads include left-handed threads and right-handed threads. In an embodiment, the threads on both of the first screw shaft 50 and the second screw 30 are either right-handed or left-handed threads so that the first screw shaft 50 will become fixed into the second screw 30 while the first screw 20 is tightened into place within the second screw 30.

Figure 2:
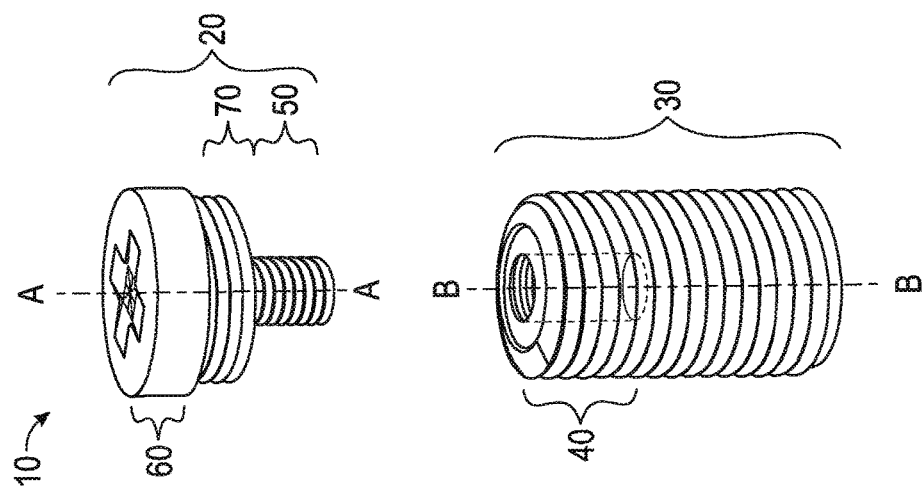
FIG. 2 is a side view of the assembly of the first screw and the second screw where the first screw has an adaptable head, according to another embodiment of the invention.

Referring to FIG. 2, in an embodiment, the first screw 20 further comprises an adaptable screw head 60. The adaptable screw head 60 is adapted to accommodate a secondary screw head 70 by combining the secondary screw head 70 with the first screw shaft 50, which allows the design of the screw head to be made compatible with existing screw head products. Alternatively, the first screw 20 and/or the article 10 is adapted to interface with a bone plate (not shown).

Figure 3:
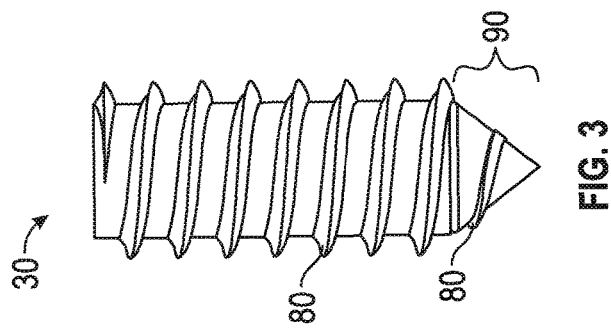
FIG. 3 is a side view of the second screw according to another embodiment of the invention.

Referring to FIG. 3, in an embodiment, the second screw 30 has a conically shaped end 90 opposite the end that is in contact with the first screw 20. The conically shaped end 90 is also threaded. The conically shaped end 90 of the second screw 30 assists with implementation of the article 10 in a living being during a self-tapping process.

In an embodiment, the article 10 can be molded entirely from the biodegradable composition, and hence is wholly biodegradable. In another embodiment, the article 10 comprises and/or is molded from a non-biodegradable composition, and hence is partially biodegradable. In yet another embodiment, the biodegradable composition is at least one coating applied to at least a portion of the first and/or second screw.

The biodegradable composition comprises a metal or a metal alloy, where the metal or metal alloy comprises calcium, strontium, zinc, magnesium or a combination comprising at least one of the foregoing. In an embodiment, the metal alloy comprises two or more elements where at least one element is calcium, strontium, zinc or magnesium.

In yet another embodiment, the metal alloy comprises 3 or more elements (i.e., it is a ternary alloy). In one embodiment, the metal alloy comprises 4 or more elements. In another embodiment, the metal alloy comprises 5 or more elements. In an exemplary embodiment, the metal alloy comprises of 3 or more elements. The metal alloy comprises a base metal, a second element and a third element. The metal alloy has the formula (1) shown below:

$$M_x M_y M_z \qquad (1)$$

where $M_x$ is a base metal, $M_y$ is a second element and $M_z$ is a third element, where x, y and z represent the weight fractions of the respective metals in the metal alloy and where the sum of x, y and z is equal to 100% (if measured in terms of a percentage) or 1 (if measured in terms of a fraction). For example, if the base metal constitutes 70 weight percent (wt %) of the metal alloy, the second element constitutes 20 wt % of the metal alloy and the third element constitutes 10 wt % of the metal alloy, then x=0.7, y=0.2 and z=0.1 and the sum of x, y and z=1 or x=70%, y=20% and z=10% and the sum of x, y and z=100%. It is to be noted that the second and the third elements are metals.

The base metal is that metal that is present in the metal alloy in the largest amount. The base metal comprises magnesium, calcium, zinc, strontium, or a combination comprising at least one of the foregoing base metals. The base metal is present in the metal alloy in an amount of about 40 to about 99 wt %, specifically about 50 to 98 wt %, and more specifically about 60 to about 97 wt %, based on the total weight of the metal alloy. An exemplary base metal is magnesium.

The second element and the third element are different in composition from each other and are selected from the group consisting of scandium, yttrium, gadolinium, cerium neodymium, dysprosium, or a combination thereof.

The second element is present in an amount of about 0.5 to about 40 wt %, specifically about 0.5 to 20 wt %, and more specifically about 1.0 to about 5 wt %, based on the total weight of the metal alloy. In an exemplary embodiment, the second element is scandium.

The third element is present in an amount of about 0.1 to about 20 wt %, specifically about 1 to about 8 wt %, and more specifically about 1.5 to about 4 wt %, based on the total weight of the metal alloy. In an exemplary embodiment, the third element is yttrium.

The weight ratio of the second element to the third element is about 0.2:1 to about 1:0.25, specifically about 0.5:1 to about 1:0.5, and more specifically about 0.75:1 to 1:0.75.

Minor amounts of other elements may be added to the metal alloy to refine the structure. Examples of such elements are manganese and zirconium. These elements are added in amounts of 0.1 to about 1 wt %, based on the total weight of the alloy.

In one embodiment, when magnesium is used as the base metal, scandium is used as the second element and yttrium is used as the third element. The magnesium is used in amounts of about 92 to about 96 wt %, while scandium is used in amounts of about 1.5 to about 4.0 wt %, while yttrium is used in amounts of about 1.5 to about 4.0 wt %.

The article 10 may further comprise additional elements commonly used with medical or dental implants, including, but not limited to pins, rods and/or plates. These additional elements may similarly be wholly or partially composed of the biodegradable composition, or may not include the biodegradable composition at all.

In an embodiment, at least a portion of the article 10 is coated with a plurality of nanoparticles, the plurality of nanoparticles comprising a medical treatment composition. In another embodiment, the plurality of nanoparticles have a hollow core in which the medical treatment composition is disposed and the plurality of nanoparticles are at least partially coated with the biodegradable coating composition. The plurality of nanoparticles thus facilitate the time-released, and/or targeted delivery of the medical treatment composition.

In an embodiment, the nanoparticles in the plurality of nanoparticles are randomly distributed in a coating on the article 10. In an embodiment, the nanoparticles in the plurality of nanoparticles are uniformly distributed in a coating on the article 10.

Any type or size of nanoparticle may be employed. Non-limiting examples of nanoparticles include, nanotubes, nanospheres, nanowires, and the like, or a combination comprising at least one of the foregoing. In an embodiment, the plurality of nanoparticles have an average particle size of 1 to 10,000 nm, specifically, 1 to 1,000 nm, more specifically 1 to 100 nm.

In an embodiment, in one method of manufacture, the first screw 20 and/or the second screw 30 is molded. Any suitable molding technique may be employed to mold the first screw 20 and/or the second screw 30. Non-limiting examples of molding techniques include injection molding and compression molding, In another embodiment, the first screw 20 and/or the second screw 30 is machined (e.g., using a lathe).

The article 10 is high-load-bearing. In an embodiment, the article is capable of withstanding loads of up to 200 kg, specifically up to 180 kg, more specifically up to 160 kg, and even more specifically up to 140 kg.

The article 10 has a strength which is substantially similar to that of a bone in a living being in comparison to a titanium implant. In an embodiment, the article 10 has a modulus of elasticity of at least 80 GPa, specifically at least 60 GPa, more specifically 50 GPa, and even more specifically at least 40 GPa.

The article may be employed as an orthopedic implant (e.g., a medical or a dental implant) when disposed inside a living being. The article 10 is thus capable of bearing high loads, reduces stress shielding, improves stress sharing, does not form a residual pool after degradation, is produced without specialized equipment, surface pre-treatments and/or restricted substrate geometries and/or positively influences bone growth and/or the healing process, when the article is used in the body of a living being.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

The invention claimed is:

1. A method comprising:
    molding a first screw; and
    molding a second screw, the first screw being reversibly attached to the second screw such that a longitudinal axis of the first screw coincides with or is parallel to a longitudinal axis of the second screw,
    wherein at least one of the first screw or the second screw comprises a biodegradable composition, which comprises a metal or a metal alloy comprising magnesium, strontium, zinc, calcium, or a combination comprising at least one of the foregoing, wherein at least a portion of at least one of the first screw or the second screw is coated with a plurality of nanoparticles, the plurality of nanoparticles comprising a medical treatment composition.

2. The method of claim 1, wherein at least one of the first screw or the second screw is wholly biodegradable.

3. The method of claim 1, wherein at least one of the first screw or the second screw comprises a biodegradable portion and a non-biodegradable portion.

4. The method of claim 1, wherein at least a portion of at least one of the first screw or the second screw is coated with the biodegradable composition.

5. The method of claim 1, wherein at least one of the first screw or the second screw are self-tapping.

6. The method of claim 1, wherein the first screw has a first screw head which is adapted to accommodate a second screw head.

7. The method of claim 1, wherein the first screw comprises a first screw shaft and a ratio of a diameter of the first screw shaft to an outer diameter of the second screw shaft is 0.5 to 0.8.

8. The method of claim 1, wherein a base metal is present in an amount of from 60 to 97 wt %.

9. A method comprising:
    disposing in a body of a living being an article comprising:
    a first screw; and
    a second screw, the first screw being reversibly attached to the second screw such that a longitudinal axis of the first screw coincides with or is parallel to a longitudinal axis of the second screw; and
    wherein the first screw and the second screw comprise a biodegradable composition,
    the biodegradable composition comprising a metal or metal alloy comprising magnesium, strontium, zinc and calcium, or a combination comprising at least one of the foregoing, wherein at least a portion of the article is coated with a plurality of nanoparticles, the plurality of nanoparticles comprising a medical treatment composition.

10. The method of claim 9, wherein the article is wholly biodegradable.

11. The method of claim 9, wherein the article comprises a biodegradable portion and a non-biodegradable portion.

12. The method of claim 9, wherein at least a portion of the article is coated with the biodegradable composition.

13. The method of claim 9, wherein at least one of the first screw or the second screw are self-tapping.

14. The method of claim 9, wherein the first screw has a first screw head which is adapted to accommodate a second screw head.

15. The method of claim 9, wherein the first screw comprises a first screw shaft and a ratio of a diameter of the first screw shaft to an outer diameter of the second screw shaft is 0.5 to 0.8.

16. The method of claim 9, wherein a base metal is present in an amount of from 60 to 97 wt %.

* * * * *